(12) United States Patent
Beck

(10) Patent No.: US 9,839,371 B2
(45) Date of Patent: Dec. 12, 2017

(54) METHOD AND APPARATUS FOR CAPTURE OF PHYSIOLOGICAL SIGNALS AND IMAGE DATA

(71) Applicant: Siemens Aktiengesellschaft, Munich (DE)

(72) Inventor: Thomas Beck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 15/088,743

(22) Filed: Apr. 1, 2016

(65) Prior Publication Data

US 2016/0292854 A1    Oct. 6, 2016

(30) Foreign Application Priority Data

Apr. 1, 2015   (DE) .................. 10 2015 205 937

(51) Int. Cl.
| | |
|---|---|
| *G06K 9/00* | (2006.01) |
| *A61B 5/055* | (2006.01) |
| *A61B 5/00* | (2006.01) |
| *A61B 5/113* | (2006.01) |
| *A61B 5/05* | (2006.01) |

(Continued)

(52) U.S. Cl.
CPC .............. *A61B 5/055* (2013.01); *A61B 5/113* (2013.01); *A61B 5/721* (2013.01); *G01R 33/4808* (2013.01); *A61B 5/1135* (2013.01); *G01R 33/4806* (2013.01); *G01R 33/5673* (2013.01)

(58) Field of Classification Search
USPC ......... 382/100, 103.106–107, 128, 134, 162, 382/168, 173, 181, 199, 209, 214, 219, 382/232, 254, 274–276, 286–291, 312, 382/180; 600/413, 410; 423/307; 378/4, 378/21
See application file for complete search history.

(56) References Cited

U.S. PATENT DOCUMENTS

| | | | |
|---|---|---|---|
| 6,798,199 B2 * | 9/2004 | Larson | G01R 33/5676 324/307 |
| 2004/0102693 A1 * | 5/2004 | Jenkins | A61B 6/481 600/410 |
| 2007/0067120 A1 | 3/2007 | Kasselmann et al. | |

(Continued)

OTHER PUBLICATIONS

Glover et al., "Image-Based Method for Retrospective Correction of Physiological Motion Effects in fMRI: RETROICOR," Magnetic Resonance in Medicine, vol. 44, pp. 162-167 (2000).

(Continued)

*Primary Examiner* — Seyed Azarian
(74) *Attorney, Agent, or Firm* — Schiff Hardin LLP

(57) ABSTRACT

In a method and an image capturing system (5) for capturing signals and image data of a volume segment of an examination object, raw data of the volume segment are captured, and image time stamps are captured at which certain of the raw data are captured. Physiological signals of the examination object are captured at the same time as capturing the raw data. Signal time stamps are captured at which certain of the physiological signals are captured. The capture of the raw data and the capture of the physiological signals is controlled by the same processor of the image capturing system, so that both the image time stamps and the signal time stamps are predetermined by the same processor.

11 Claims, 3 Drawing Sheets

(51) Int. Cl.
  *G01R 33/48* (2006.01)
  *G01R 33/567* (2006.01)

(56) References Cited

U.S. PATENT DOCUMENTS

| | | | | |
|---|---|---|---|---|
| 2012/0245453 | A1* | 9/2012 | Tryggestad | A61B 6/463 600/413 |
| 2013/0035588 | A1* | 2/2013 | Shea | G01R 33/4833 600/413 |
| 2014/0334702 | A1* | 11/2014 | El Fakhri | G06T 11/005 382/131 |

OTHER PUBLICATIONS

Birn et al., "Separating respiratory-variation-related fluctuations from neuronal-activity-related fluctuations in fMRI," NeuroImage, vol. 31, pp. 1536-1548 (2006).

Beall et al., "The non-separability of physiologic noise in functional connectivity MRI with spatial ICA at 3T," Journal of Neuroscience Methods, vol. 191, pp. 263-276 (2010).

Thomason et al., "Breath holding reveals differences in fMRI BOLD signal in children and adults," NeuroImage, vol. 25, pp. 824-837 (2005).

Hutton et al., The impact of physiological noise correction on fMRI at 7T, NeuroImage, vol. 57, pp. 101-112 (2011).

Birn et al., "The effect of scan length on the reliability of resting-state fMRI connectivity estimates," NeuroImage, vol. 83, pp. 550-558 (2013).

* cited by examiner

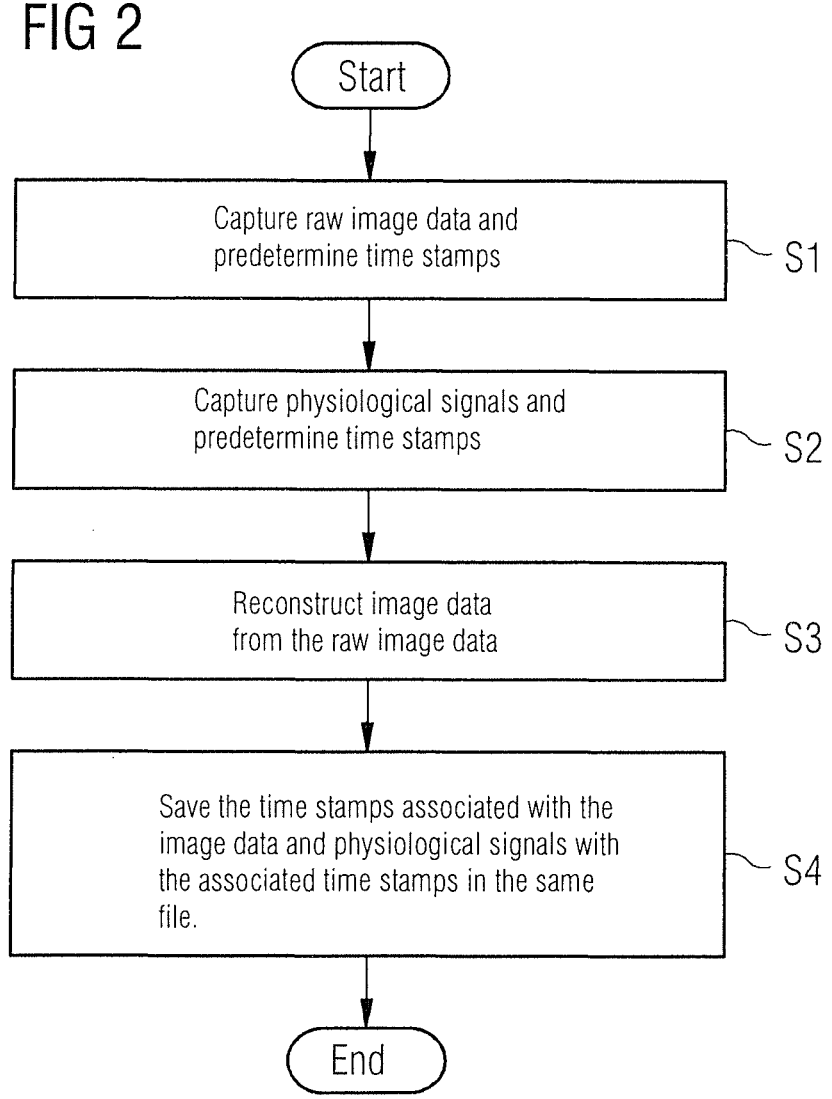

FIG 3
```xml
<PhysioData>
    <VolumeAcquisitionDescription>
        <Volume ID="0" ACQUISITION_TIME_TICS="18481544">>
            <AnatomSlice ID="0" ACQUISITION_TIME_TICS="18481544"/>
            <AnatomSlice ID="1" ACQUISITION_TIME_TICS="18482357"/>
            <AnatomSlice ID="2" ACQUISITION_TIME_TICS="18481577"/>
            <AnatomSlice ID="3" ACQUISITION_TIME_TICS="18482389"/>
            ...
            <AnatomSlice ID="47" ACQUISITION_TIME_TICS="18483104"/>
            <AnatomSlice ID="48" ACQUISITION_TIME_TICS="18482324"/>
        </Volume>
        <Volume ID="1" ACQUISITION_TIME_TICS="18483144"/>
            <AnatomSlice ID="0" ACQUISITION_TIME_TICS="18483144"/>
            <AnatomSlice ID="1" ACQUISITION_TIME_TICS="18483957"/>
            ...
            <AnatomSlice ID="47" ACQUISITION_TIME_TICS="18484704"/>
            <AnatomSlice ID="48" ACQUISITION_TIME_TICS="18483924"/>
        </Volume>
        ...
        <Volume ID="59" ACQUISITION_TIME_TICS="18575944"/>
            <AnatomSlice ID="0" ACQUISITION_TIME_TICS="18575944"/>
            <AnatomSlice ID="1" ACQUISITION_TIME_TICS="18576757"/>
            ...
            <AnatomSlice ID="47" ACQUISITION_TIME_TICS="18577504"/>
            <AnatomSlice ID="48" ACQUISITION_TIME_TICS="18576724"/>
        </Volume>
    </VolumeAcquisitionDescription>
    <PhysioStream TYPE="PULS">
        <PMU TIME_TICS="18476111" DATA="2013"/>
        <PMU TIME_TICS="18476113" DATA="1993"/>
        <PMU TIME_TICS="18476115" DATA="1978"/>
        <PMU TIME_TICS="18476117" DATA="1964"/>
        <PMU TIME_TICS="18476119" DATA="1950"/>
        <PMU TIME_TICS="18476121" DATA="1941"/>
        <PMU TIME_TICS="18476123" DATA="1937"/>
        <PMU TIME_TICS="18476125" DATA="1936"/>
        <PMU TIME_TICS="18476127" DATA="1936"/>>
        <PMU TIME_TICS="18476129" DATA="1937"/>
        <PMU TIME_TICS="18476131" DATA="1936"/>
        ...
        <PMU TIME_TICS="18479984" DATA="2860"/>
        <PMU TIME_TICS="18479986" DATA="2858"/> SIGNAL="536870912"/>
        <PMU TIME_TICS="18479988" DATA="2852"/>
        ...
    </PhysioStream>
    <PhysioStream TYPE="RESP">
        <PMU TIME_TICS="18476111" DATA="1149"/>
        <PMU TIME_TICS="18476119" DATA="1105"/>
        <PMU TIME_TICS="18476127" DATA="1047"/>
        <PMU TIME_TICS="18476135" DATA="989"/>
        <PMU TIME_TICS="18476143" DATA="960"/>
        <PMU TIME_TICS="18476150" DATA="917"/>
        <PMU TIME_TICS="18476158" DATA="888"/>
        <PMU TIME_TICS="18476166" DATA="859"/>
        <PMU TIME_TICS="18476174" DATA="859"/>
        <PMU TIME_TICS="18476182" DATA="844"/>
        <PMU TIME_TICS="18476190" DATA="844"/>
        <PMU TIME_TICS="18476198" DATA="830"/>
        <PMU TIME_TICS="18476206" DATA="873"/>
        <PMU TIME_TICS="18476214" DATA="902"/>
        ...
    </PhysioStream>
    ...
</PhysioData>
```

METHOD AND APPARATUS FOR CAPTURE OF PHYSIOLOGICAL SIGNALS AND IMAGE DATA

BACKGROUND OF THE INVENTION

Field of the Invention

The present invention concerns a method and an image capturing system for simultaneously capturing physiological signals and (raw) image data of a volume segment of an examination object.

Description of the Prior Art

US 2004/0102693 A1 describes a method of synchronizing image data with physiological data, by time stamps being used during the capture of image data, the time stamps being generated by a first clock, and by time stamps being used during the capture of physiological data, these time stamps being generated by a second clock.

DE 60 2005 005 924 T2 describes a uniform data format for measuring devices.

With functional tomography, physiological functions in the inside of a living examination object are displayed with the aid of an imaging method. Functional magnetic resonance tomography is especially known here, with which, in particular based on the blood oxygenation (BOLD effect), activated brain areas of the examination object can be displayed with a high spatial resolution. However a dynamic heart tomography examination, a time-resolved tomography examination of joint movements or a perfusion tomography examination (i.e. the display of blood flow in organs and tissue) also form part of the field of functional tomography.

The evaluation of functional tomography is significantly influenced here by physiological (interference) signals such as for instance breathing or heartbeat. In particular, breathing causes an unwanted influence on the oxygen saturation of the blood and is consequently considered to be an interference variable, which negatively affects statistical results of the functional tomography.

In a functional MR tomography examination, an unwanted, physiologically induced signal change can contribute up to 60% to a variance and thus can considerably influence the sensitivity of results (i.e. result images). It must be taken into account here that in the case of functional MR tomography the portion of physiological interference signals grows with an increasing magnetic field strength. Since functional MR tomography is currently almost exclusively performed with field strengths of 3 Tesla or more, consideration of the physiological signals while evaluating the results of a functional MR tomography examination is of decisive importance.

SUMMARY OF THE INVENTION

An object of the present invention is to improve the capture of physiological signals and image data compared with the prior art in order, as a result, to improve the evaluation of a functional tomography examination in particular.

Within the scope of the present invention, a method is provided for capturing physiological signals of a living examination object and image data of a volume segment of the examination object with the same image capturing system (e.g. the same magnetic resonance system). The method includes the following steps.

Raw data of the volume segment are captured with a raw data scanner. When the scanner is a magnetic resonance scanner, the raw data are entered into an electronic memory as k-space data, in a portion of k-space that corresponds to the volume segment to be imaged, such as slice-by-slice of the volume segment.

Image time stamps are also captured, with each image time stamp specifying the time instant at which certain of the raw data are captured.

At the same time as capturing the raw data, physiological signals of the examination object are captured.

Signal time stamps are also captured, with each signal time stamp specifying the time instant at which a certain signal of the physiological signals is captured.

The capture of raw data and the capture of physiological signals are controlled by the same processor of the image acquisition system, so that both the image time stamps and also the signal time stamps are predetermined by the same processor. In other words, only the same timer (namely the processor) is used both as a clock generator or timer for capturing the raw data and for capturing or predetermining the image time stamps, and as a clock generator or timer for capturing the physiological signals and for capturing or predetermining the signal time stamps. In other words, an apparatus with its own timer is not used to capture the physiological signals, as is the case according to the prior art.

Since only one clock generator is used to capture the raw data and the physiological signals and to predetermine the image time stamps and the signal time stamps, a synchronization of a number of timers or clock generators is advantageously avoided.

Each image time stamp represents a specification of a time instant at which the associated raw data are captured, as well as an information datum by which the image data reconstructed from the associated raw data can be identified. A signal time stamp represents the specification of a time instant at which the associated physiological signal is captured, as well as the value of the associated physiological signal itself.

An associated time stamp is preferably captured for each physiological signal.

According to a preferred embodiment of the invention, the raw data are captured slice-by-slice with a magnetic resonance data acquisition scanner. An image time stamp is predetermined here for each captured slice, this image time stamp specifying the time instant at which the raw data of the corresponding slice are captured. If the time taken to capture the raw data of a slice plays a role in the accuracy of the time stamps, the image time stamp captured for the respective slice can describe the time instant for instance at which capture of the raw data of that slice was started.

The image capturing system can be a medical imaging device for capturing, processing, evaluating and/or saving image information. In order to capture raw data or image information, the image capturing system can use acoustic methods, which capture ultrasound for instance, or emission methods, such as e.g. emission computed tomography (ECT) and positron emission tomography (PET), or optical methods or radiological methods, such as e.g. x-ray tomography or computed tomography (CT), or MR tomography, as well as combinations of these methods.

The capture of physiological signals can either be the capture of physiological signals from just one source of physiological signals, or the capture of physiological signals from a number of sources of physiological signals. In either case, each source of physiological signals is controlled by the same clock generator or by the same processor of the image capturing system, so that all signal time stamps are predetermined by the same clock generator.

Examples of a source of physiological signals here are a respiratory belt, a pulse monitor or a blood pressure monitor.

The inventive method can include a reconstruction of image data from the raw data.

This variant offers the decisive advantage that both the raw data from which the image data are reconstructed, and the physiological signals in the same processing chain (e.g. of the same image capturing system), are processed. The image data thus can be reconstructed from the raw data as a function of the physiological signals.

If images of the volume segment are captured for instance for a functional tomography examination at a number of time instants, timing changes (i.e. changes over time) within the volume segment can be captured on the basis of these images or image data as a function of the physiological signals captured at the same time, before the last raw data have been captured.

Since the raw data and the physiological signals are captured by the same image capturing system, the physiological signals are immediately available so that on the basis of the physiological signals, the timing changes within the volume segment, which also result in corresponding changes to the image data, can still be captured during the capture of the raw data. As a result, it is possible for instance to stop the procedure early if, on the basis of the physiological signals, it is recognized that the timing changes within the volume segment exceed a tolerable threshold value. Such an approach is not possible for instance if the physiological signals are only available after the raw data has been captured.

For instance, in examination known as 'resting state' examinations, on the basis of the physiological signals immediately available, the present invention allows physiological noise, which results in incorrectly detected connectivities, to be recognized during the measurement itself, so that the measurement can be stopped early.

In a preferred embodiment, the method includes the following further steps.

The image time stamps associated with the reconstructed image data are saved in a predetermined data format. In doing so, the respective image time stamp of the reconstructed image data corresponds in each case to the image time stamp which forms part of the raw data from which the respective image data has been reconstructed.

The signal time stamps including the associated physiological signals in the same data format are also saved. In other words, the physiological signals, the signal time stamps and the image time stamps are all saved in the same data format.

In this embodiment, each image time stamp and each signal time stamp is saved in each case as an independent entry in the data format.

Since each image time stamp and each signal time stamp is saved together with the associated physiological signal and since each time stamp is predetermined by the same clock generator or by the same processor, a drift in the physiological signals in respect of the image data (i.e. a timing shift in the signal time stamps compared with the image time stamps) advantageously cannot occur.

The XML format (Extensible Markup Language) is used in particular as the same predetermined data format.

According to a preferred inventive embodiment, a specific target data format can be predetermined, in which the physiological signals are to be saved with the respective signal time stamps and/or the image time stamps (in some instances including the associated reconstructed image data). Here the physiological signals are saved in the target data format with the respective signal time stamps and/or the image time stamps, which are saved together in the predetermined data format (in some instances including the associated reconstructed image data).

An advantage of the present invention is that the physiological signals with the associated time stamps and the image time stamps, through which the associated reconstructed image data can be determined, are saved in the predetermined data format (preferably XML) such that the physiological signals, the signal time stamps and the image time stamps (and in some instances also the associated reconstructed image data) can then be transferred in any formats. As a result, at the point in time of capturing (and saving) the raw data and the physiological signals, it is not yet necessary to define which raw data are relevant to a subsequent evaluation and in which format the raw data are to be saved for the subsequent evaluation.

Within the scope of the present invention, an image capturing system is also provided to capture physiological signals of a living examination object and image data of a volume segment of the examination object. Here the image capturing system has a processor for actuating a scanner to capture raw data of the volume segment and to capture or predetermine image time stamps, which specify in each case the time instant at which the associated raw data are captured. Moreover, at the same time as capturing the raw data with the same processor, the image capturing system is designed to capture physiological signals of the examination object and associated signal time stamps, which specify the time instant at which the associated physiological signals are captured. The same processor therefore predetermines both the image time stamps and the signal time stamps.

The advantages of the inventive image capturing system correspond here substantially to the advantages of the inventive method, which have been cited above in detail.

Furthermore the present invention encompasses a non-transitory data storage medium encoded with programming instructions (code) such as a computer program or software, which can be loaded in a memory of a programmable controller or a computer of an image capturing system. All or various above-described embodiments of the inventive method can be implemented when program code is executed in the controller or computer of the image capturing system. The program code may possibly require program support, e.g. libraries and auxiliary functions, in order to realize the corresponding embodiments of the method. The program code may be a source code (e.g. C++) which must still be compiled and linked or which only has to be interpreted, or an executable software code, which for execution purposes only has to be loaded into the corresponding computer or controller.

The electronically readable data carrier may be a DVD, a magnetic tape, a hard disk or a USB stick, on which electronically readable code, in particular software (cf. above), is stored.

The present invention allows for an exact correspondence between the captured image data and the simultaneously measured physiological signals, which is also referred to as mapping of the physiological signals to the image data and represents a central point when the image data are corrected for physiological influences.

BRIEF DESCRIPTION OF THE DRAWINGS

FIG. 2 is a flowchart of an embodiment of the inventive method.

FIG. 3 shows an example in accordance with the invention in which data is saved in XML format.

DESCRIPTION OF THE PREFERRED EMBODIMENTS

Figure 1:
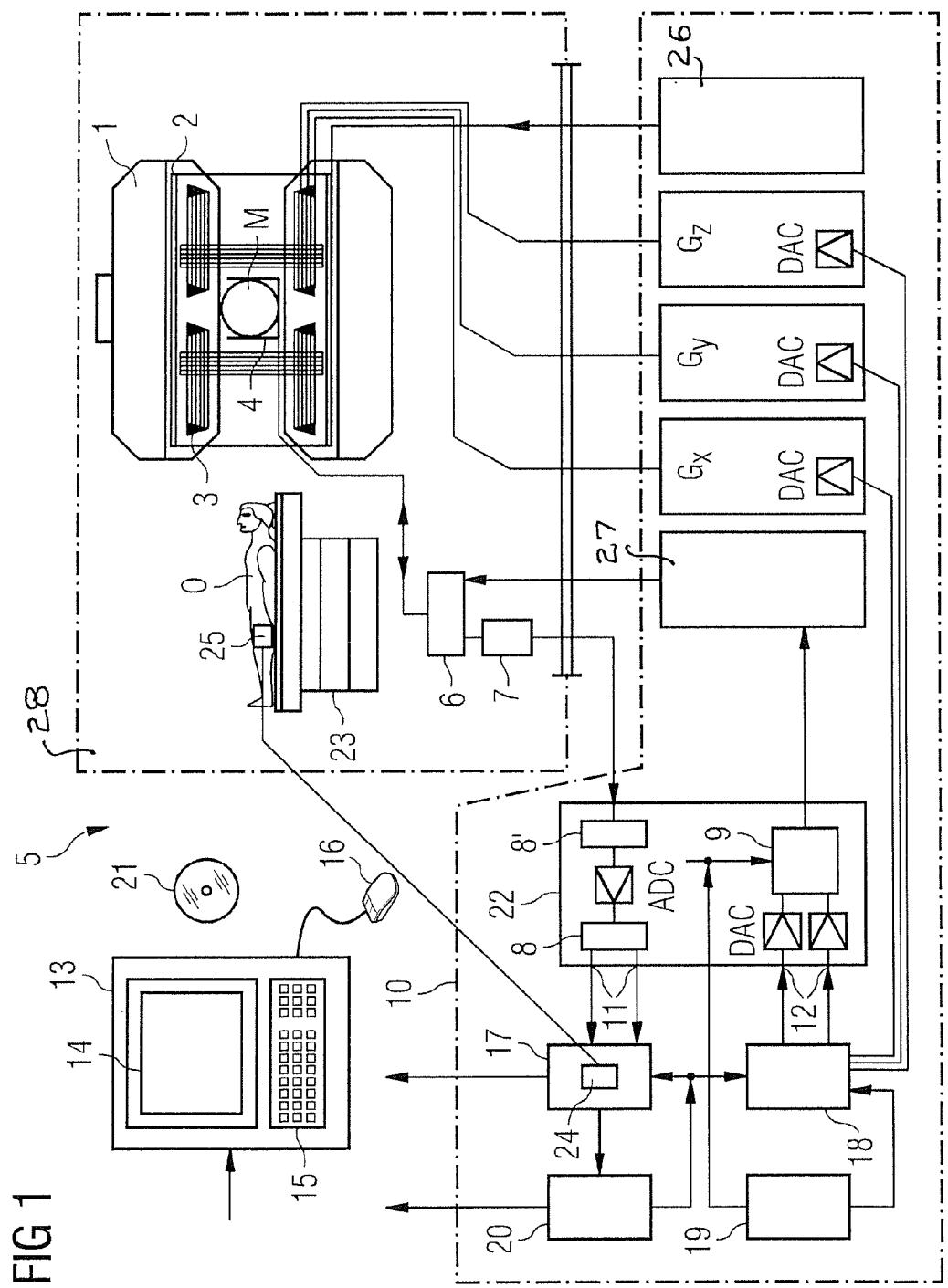
FIG. 1 schematically illustrates a magnetic resonance system as an example of an inventive image capturing system.

FIG. 1 is a schematic illustration of a magnetic resonance apparatus 5 (a magnetic resonance imaging or nuclear spin tomography apparatus) that has a magnetic resonance data acquisition scanner 28 as an example of an inventive image capturing system. Here a basic field magnet 1 generates a strong magnetic field, which is constant over time for polarization or alignment of the nuclear spins in an examination area of an object O, such as for example a part to be examined of a human body, which is examined resting on a bed 23 in the magnetic resonance system 5. The high homogeneity of the basic magnetic field required for the nuclear spin resonance measurement is defined in a typically spherical measurement volume M, in which the volume segment of the human body to be examined is arranged. To assist the homogeneity requirements and in particular to eliminate influences that are invariable over time, shim plates made of ferromagnetic material are attached at a suitable point. Influences that are variable over time are eliminated by shim coils 2, operated via a shim coils amplifier 26.

A cylindrical gradient field system or a gradient field system 3 composed of three sub-windings is used in the basic field magnet 1. Each sub-winding is supplied with power from an amplifier in order to generate a linear (also variable over time) gradient field in a respective direction of the Cartesian coordinate system. The first sub-winding of the gradient field system 3 generates a gradient $G_x$ in the x-direction, the second sub-winding a gradient $G_y$ in the y-direction and the third sub-winding a gradient $G_x$ in the z-direction. Each amplifier has a digital-to-analog converter, which is actuated by a sequence controller 18 for the timely generation of gradient pulses.

Within the gradient field system 3 is disposed one (or a number of) radio-frequency antenna(e) 4, which convert the radio-frequency pulses emitted by a radio-frequency power amplifier 27 into a magnetic alternating field in order to excite the nuclei and align the nuclear spins of the object O to be examined or the region to be examined of the object O. Each radio-frequency antenna 4 is formed by one or a number of RF transmit coils and one or a number of RF receive coils in the form of an annular, preferably linear or matrix-shaped arrangement of component coils. The alternating field emanating from the precessing nuclear spins, i.e. generally the nuclear spin echo signals produced by a pulse sequence of one or a number of radio-frequency pulses and one or a number of gradient pulses, is also converted into a voltage (measuring signal) by the RF receive coils of the respective radio-frequency antenna 4. This voltage is fed via an amplifier 7 to a radio-frequency reception channel 8 of a radio-frequency system 22. The radio-frequency system 22, which is part of a control computer 10 of the magnetic resonance system 5, further has a transmit channel 9 in which the radio-frequency pulses are generated in order to excite the magnetic nuclear resonance. The respective radio-frequency pulses are shown here digitally as a series of complex numbers on the basis of a pulse sequence in the sequence controller 18, which is predetermined by the system computer 20. This number sequence is fed as a real part and an imaginary part, via respective inputs 12, to a digital-to-analog converter in the radio-frequency system 22 and from this to a transmit channel 9. In the transmit channel 9, the pulse sequences are modulated onto a radio-frequency carrier signal, the basic frequency of which corresponds to the resonance frequency of the nuclear spins in the measuring volume.

The switchover from transmit mode to reception mode takes place way of a transmit/receive switch 6. The RF transmit coils of the radio-frequency antenna(e) 4 radiate the radio-frequency pulses into the measuring volume M to excite the nuclear spins and resulting echo signals are scanned by way of the RF receive coil(s). The correspondingly obtained nuclear resonance signals are demodulated in the receive channel 8' (first demodulator) of the radio-frequency system 22 in a phase-sensitive manner to an intermediate frequency, digitalized in the analog-to-digital converter (ADC) and output by way of the output 11. This signal is demodulated to the frequency 0. The demodulation to the frequency 0 and the separation into real and imaginary parts takes place after digitalization in the digital domain in a second demodulator 8. Using an image processor 17 an MR image is reconstructed from the measurement data obtained in this manner via an output 11. Administration of the measurement data, image data and control programs takes place with the system processor 20. On the basis of a specification with control programs, the sequence controller 18 controls the generation of the respectively desired pulse sequences and the corresponding scanning of k-space. Here the sequence controller 18 controls the timely switching of the gradients, the transmission of the radio-frequency pulses with a defined phase amplitude and the receipt of the nuclear resonance signals. The time base for the radio-frequency system 22 and the sequence controller 18 is provided by a synthesizer 19. The selection of corresponding control programs for generating an MR image, which are stored e.g. on a DVD 21, and the display of the generated MR image takes place by way of a terminal 13, which comprises a keyboard 15, a mouse 16 and a monitor 14.

Moreover, the magnetic resonance system 5 has a pulse monitor 25, with which a pulse of the examination object O is captured at the same time as the echo signals or raw data are captured. Control of this pulse monitor 25 and control of the capture of the echo signals or raw data occurs here by a timer 24 of the image processor 17, wherein this timer 24 predetermines both the signal time stamps per captured physiological signal (in this case per captured pulse value) and also the image time stamps per captured raw data. The timer 24 thus also controls the sequence controller 18.

FIG. 2 shows the flowchart of an embodiment of the inventive method.

In step S1, the raw data of a volume segment of an examination object are captured, wherein image time stamps are predetermined, which each specify the time instant at which the associated raw data were captured. Physiological signals of the examination object are captured in step S2 at the same time as step S1 and signal time stamps are predetermined, which each specify the time instant at which the associated physiological signal was captured. It is important that control of both the capture of the raw data and the capture of the physiological signals is performed by the same processor, so that both the image time stamps and also the signal time stamps are predetermined by the same clock generator or the same processor.

The image data are reconstructed in step S3 from the raw data. Since the physiological signals and the raw data are captured by the same image capturing system, which also performs the reconstruction of the image data, the reconstructed image data can be evaluated immediately as a function of the physiological signals.

In step S4, the image time stamps associated with the image data and the physiological signals with the associated signal time stamps are saved in the same format (preferably XML) in the same file.

FIG. 3 shows the portion of a file, in which the captured physiological signals with their associated signal time stamps and image time stamps are saved in XML format in accordance with the invention.

The inventive saving procedure advantageously allows for a direct assignment to be established between the physiological information or signals and the image data. This file can then be transferred into a DICOM-compliant structure for long-term storage of the data contained in the file in an image database or in what is known as a PACS ("Picture Archiving and Communication System"). The reconstructed image data are also then saved in this image database or in this PACS in a form in particular in which the respective image data can be assigned to the associated image time stamps.

Image time stamps are disposed in the first part of the file which is introduced by 'VolumeAcquisitionDescription'. There are image time stamps here on the one hand which each specify the time instant at which a (new) capture of the raw data of the volume segment is started and there are image time stamps which each specify the time instant at which the capture of the raw data of a certain layer of the volume segment is started. The time instant is specified with each time stamp in ticks since midnight, wherein one tick corresponds to 2.5 ms.

In the second part of the file, which is introduced by 'PhysioStream TYPE', the physiological data or signals are described. Here each physiological channel (i.e. each source of physiological signals) is encoded separately in a 'PhysioStream' and each data point, aside from its associated signal time stamp, comprises the physiological measured value and optionally one 'SIGNAL'. The signal can be used to initiate a specific measurement at, in physiological terms in each case identical, time instants (e.g. with each identical state of the heart cycle). When image data are captured for a functional tomography examination, the measurement nevertheless is generally not time-dependent in relation to specific signals, but is instead carried out continuously.

Advantageously, the saving of physiological signals shown in FIG. 3 allows physiological signals from a number of sources of physiological signals (i.e. from several physiological channels) to be saved together, even if the physiological signals are scanned with different scanning frequencies. For instance, according to FIG. 3, the physiological signals of type 'PULSE' (i.e. the pulse of the examination object) are scanned at an interval of 5 ms (corresponding to two ticks), while the physiological signals of type 'RESP' (the breathing of the examination object) are captured at an interval of 20 ms (corresponding to 7 or 8 ticks).

On the basis of the inventive format of saving shown in FIG. 3, any acquisition sequences of layers of the volume segment can also be stored, since the time instant at which the raw data of this layer was captured is specified for each layer by way of the associated image time stamp. For instance, the 49 layers of 60 volumes in FIG. 3 are scanned nested by the layers in the sequence ID="0", "2", "4", . . . , "48", "1", "3", . . . , "47" being scanned first for each volume, as is apparent from the time specification in each time stamp. Each of the 60 volumes describes here the predetermined volume segment and in a sense merges the image data of its 49 layers, which were captured from the volume segment within a respectively determined time interval.

The XML description of a measurement shown in FIG. 3 can be saved in an image database as what is known as a non-image DICOM (Digital Imaging and Communications in Medicine), in which in particular the associated reconstructed image data are also saved in the DICOM standard. In what is referred to as the DICOM Tag of the non-image DICOM, in which the XML description is saved, aside from a precise description of the measurement or capture of the raw data, a large amount of information relating to this measurement can be contained. The name and other data of the examination object can be stored inter alia.

The data saved in the XML format in accordance with the invention, as is shown by way of example in FIG. 3, can be transferred into any text-type display of specific information contained in the saved data. A user-defined XSLT style sheet can be used to this end for instance. In other words, at any time instant after capturing and saving the image data and physiological signals, it is possible to define which physiological information is required for an evaluation. As a function of this, a suitable conversion of the inventively saved data can then take place in order to convert this into a desired target format. As a result, existing and inventively saved data can also be evaluated for instance by future, novel evaluation methods, without the data having to be captured again.

Saving the physiological signals in the image database as a (non-image) DICOM image in summary has the following advantages.

No manual file management is required, since the physiological signals are saved directly together with the image data.

The physiological signals can be assigned directly to the image data so that a future automated processing of the physiological signals is also supported.

Further information relating for instance to the capture of data and the examination object can be stored in the non-image DICOM image.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring physiological signals and raw data for imaging of a volume segment of an examination subject, comprising:

from a computer that operates according to a computer time base, operating a medical raw data scanner to acquire medical raw data for imaging of a volume segment of a subject situated in the scanner and acquiring image time stamps at which at least some of the raw data are acquired;

from said computer operating according to said computer time base, operating a physiological sensor to acquire physiological signals from the examination subject simultaneously with acquiring said raw data, and acquiring signal time stamps at which at least some of the physiological signals are acquired;

storing said image time stamps in a predetermined data format in an electronic memory;

storing said physiological signals and the associated time stamps also in the same data format, with each image time stamp and each signal time stamp being stored as an independent entry in said data format; and making the acquired raw data and physiological signals, and the respective image time stamps and signal time stamps available from the electronic memory, via the computer, in electronic form as a data file.

2. A method as claimed in claim 1 comprising operating said physiological sensor from said computer to acquire a time stamp for each acquired physiological signal.

3. A method as claimed in claim 1 comprising operating the scanner from said computer to acquire said raw data in a plurality of successive slices of said volume segment, and acquiring a respective image time stamp for each acquired slice at a time at which the raw data of the respective slice are acquired.

4. A method as claimed in claim 1 comprising using a magnetic resonance scanner as said medical raw data acquisition scanner.

5. A method as claimed in claim 1 comprising acquiring said physiological signals from a plurality of different sources of physiological signals simultaneously.

6. A method as claimed in claim 1 comprising, in a reconstruction computer, executing a reconstruction algorithm to reconstruct image data from said raw data.

7. A method as claimed in claim 6 comprising acquiring timing changes within said volume segment based on said image data dependent on said physiological signals before a last of said raw data are acquired.

8. A method as claimed in claim 1 comprising employing the Extensible Markup Language (XML) format as said data format.

9. A method as claimed in claim 1 comprising predetermining a specific target data format, in which the physiological signals with at least one of the associated signal time stamps or image time stamps are to be stored, and storing the physiological signals with the associated at least one of the signal time stamps and image time stamps in said target data format.

10. A medical image data acquisition system comprising:
a medical raw data acquisition scanner;
a physiological sensor;
an electronic memory;
a computer configured to operate according to a computer time base, said computer being configured to operate said medical raw data scanner to acquire medical raw data for imaging of a volume segment of a subject situated in the scanner and to acquire image time stamps at which at least some of the raw data are acquired;

said computer, operating according to said computer time base, being configured to operate the physiological sensor to acquire physiological signals from the examination subject simultaneously with acquiring said raw data, and to acquire signal time stamps at which at least some of the physiological signals are acquired;
said computer being configured to store said image time stamps in a predetermined data format in said electronic memory;
said computer being configured to store said physiological signals and the associated time stamps also in the same data format, with each image time stamp and each signal time stamp being stored as an independent entry in said data format; and
said computer being configured to make the acquired raw data and physiological signals, and the respective image time stamps and signal time stamps available from the electronic memory in electronic form as a data file.

11. A non-transitory, computer-readable data storage medium encoded with programming instructions, said storage medium being loaded into a control computer of a medical raw data acquisition system that comprises a medical raw data acquisition scanner and a physiological sensor, and said programming instructions causing said control computer to:
operate according to a computer time base to operate the medical raw data scanner to acquire medical raw data for imaging of a volume segment of a subject situated in the scanner and to acquire image time stamps at which at least some of the raw data are acquired;
operate according to said computer time base to operate the physiological sensor to acquire physiological signals from the examination subject simultaneously with acquiring said raw data, and acquire signal time stamps at which at least some of the physiological signals are acquired;
store said image time stamps in a predetermined data format in an electronic memory;
store said physiological signals and the associated time stamps also in the same data format, with each image time stamp and each signal time stamp being stored as an independent entry in said data format; and
make the acquired raw data and physiological signals, and the respective image time stamps and signal time stamps available from the electronic memory in electronic form as a data file.

* * * * *